US011998423B2

United States Patent
Murakami

(10) Patent No.: US 11,998,423 B2
(45) Date of Patent: Jun. 4, 2024

(54) LIQUID ADMINISTRATION TOOL

(71) Applicant: HUNDRED CO., LTD., Koriyama Fukushima (JP)

(72) Inventor: Makoto Murakami, Sukagawa Fukushima (JP)

(73) Assignee: HUNDRED CO, LTD., Fukushima (JP)

( * ) Notice: Subject to any disclaimer, the term of this patent is extended or adjusted under 35 U.S.C. 154(b) by 1193 days.

(21) Appl. No.: 16/626,222

(22) PCT Filed: Jun. 28, 2017

(86) PCT No.: PCT/JP2017/023812
§ 371 (c)(1),
(2) Date: Jul. 7, 2020

(87) PCT Pub. No.: WO2019/003358
PCT Pub. Date: Jan. 3, 2019

(65) Prior Publication Data
US 2020/0405466 A1    Dec. 31, 2020

(51) Int. Cl.
*A61B 5/15*      (2006.01)
*A61D 7/00*     (2006.01)
(Continued)

(52) U.S. Cl.
CPC .......... *A61D 7/00* (2013.01); *A61B 5/150404* (2013.01); *A61B 5/15074* (2013.01);
(Continued)

(58) Field of Classification Search
CPC .......... A61B 5/150404; A61B 5/15074; A61B 2503/40; A61B 2503/42; A61B 5/150343;
(Continued)

(56) References Cited

U.S. PATENT DOCUMENTS 1,175,108 A * 3/1916 Abelmann .............. A61M 5/32
604/239
1,503,399 A * 7/1924 Webb ...................... A61M 5/32
604/273
(Continued)

FOREIGN PATENT DOCUMENTS

JP    2001137266    5/2001
JP    2006223334    8/2006
(Continued)

OTHER PUBLICATIONS

International Search Report for International Patent Application No. PCT/JP2017/023812, dated Sep. 4, 2017.

*Primary Examiner* — Jacqueline Cheng
*Assistant Examiner* — Tho Q Tran
(74) *Attorney, Agent, or Firm* — Greer, Burns & Crain, Ltd

(57) ABSTRACT

Provided is a device that includes: a hollow needle; a fixing part that is fixed on the outer periphery of the proximal end of the needle; a connecting pipe to be attached to the protruding part that protrudes from the fixing part to the side thereof that is opposite to the needle, and that can be communicated with the needle, wherein the pipe is configured such that the distal end of the syringe can be fitted to the pipe from the side thereof that is opposite to the needle; and a holding part that protrudes outward from the outer peripheral surface of the fixing part. The connecting pipe is configured such that a hematocrit tube can be fit to the inside of the pipe from the side thereof that is opposite to the needle.

8 Claims, 4 Drawing Sheets

(51) Int. Cl.
*A61M 5/31* (2006.01)
*A61M 5/32* (2006.01)

(52) U.S. Cl.
CPC ............ *A61M 5/3137* (2013.01); *A61M 5/32* (2013.01); *A61B 2503/40* (2013.01); *A61B 2503/42* (2013.01); *A61M 2250/00* (2013.01)

(58) Field of Classification Search
CPC ...... A61B 5/150419; A61B 5/15; A61D 7/00; A61M 5/3137; A61M 5/32; A61M 2250/00; A61M 5/3287; A61M 2205/586; A61M 25/0014
See application file for complete search history.

(56) References Cited

U.S. PATENT DOCUMENTS

| | | | |
|---|---|---|---|
| 4,834,708 A * | 5/1989 | Pillari | ............... A61M 25/0637 604/165.04 |
| 2003/0181869 A1 | 9/2003 | Swenson et al. | |
| 2009/0202616 A1 * | 8/2009 | Chong | ................... A61P 17/02 424/447 |

FOREIGN PATENT DOCUMENTS

| | | |
|---|---|---|
| JP | 3134857 | 8/2007 |
| JP | 2008229313 | 10/2008 |

* cited by examiner

LIQUID ADMINISTRATION TOOL

TECHNICAL FIELD

The present invention relates to a device for injecting a liquid in to a small animal.

BACKGROUND

Administration of drugs to small animals such as experimental animals including rats, mice, rabbits, and the like is carried out by using a liquid-administration device, such as a probe or an injector. Methods of administration include oral administration, subcutaneous administration, intraperitoneal administration, intravenous administration, and intramuscular administration.

An injector used for administration has been configured such that, for example, as shown in FIG. 1, an injection needle 2 is connected to the distal end 1a of a syringe 1 that is held such that the injection needle 2 is horizontal, and in the state where the pointed part 2a of the injection needle 2 is on the lower edge of the needle 2, the needle 2 is injected into an appropriate position of an object. Then, the piston 3 is pressed, so that a drug solution is ejected out of the outer cylinder 4.

The following Patent Document 1 is a technical document that relates to a liquid-administration device of this type.

PRIOR-ART DOCUMENT

Patent Document

Patent Document 1: WO 2012/111539

SUMMARY

If, as mentioned above, a liquid is injected into small animals, the administration is a more delicate work compared with the administration of a liquid into human beings or large domestic animals. Because the object of the administration is small, using a small instrument that corresponds to the object size is a requisite. Moreover, precise operations tend to be disturbed by rubber gloves that often are worn at the time of injection. Also, if the object is moving it must be restrained or immobilized. When an injection is carried out, a moving object must be restrained by being held with one hand, and the small injector and small injection needle need to be operated with the other hand. To accurately perform this operation in a short time requires experience and skill by a user.

In particular, when intravenous administration to small animals is carried out, the aforesaid problems become significant. In carrying out intravenous administration, (1) a site where a blood vessel is easily visible, such as a tail for rats or mice, and ears for rabbits, must be selected, (2) the object must be restrained or immobilized, and (3) the injection needle must be accurately injected into a vein. For example, in the case of intravenous administration to a mouse, (1) the tail is fixed so as to cause engorgement of a vein, and (2) the injection needle is horizontally inserted into the vein so that the drug solution can be injected. At this time, much skill is required to align the tip of the injection needle with a small vein of the tail. As described above, it generally has been difficult to efficiently administer a liquid medicine to a small animal in a short time.

If a drug solution is administered to a human being, and not to a small animal, for example, the administration can be carried out in such a way that a butterfly needle having a holding part is inserted into a vein, so that the drug solution can be injected into the vein from a syringe that is connected to the proximal end of the butterfly needle via a tube. However, in this administration method, some of the drug solution eventually remains in the tube after injection. Therefore, this method is not appropriate for use on small animals into which a small quantity of a drug solution must be accurately administered. That fact is that a simple liquid-administration device suitable for injection to small animals has not been known.

In view of such circumstances, an objective of the present invention is to provide a liquid-administration device capable of efficiently administering a liquid medicine to a small animal in a short time.

The present invention relates to a liquid-administration device that includes (1) a hollow needle, (2) a fixing part that is fixed to the outer periphery of the proximal end of the needle, (3) a connecting pipe to be attached to a protruding part that protrudes from the fixing part to the side thereof that is opposite to the needle, and is to be communicated with the needle, wherein the connecting pipe is configured such that the distal end of a syringe can be fitted to the pipe from the side that is opposite to the needle, and (4) a holding part that protrudes outward from the outer peripheral surface of the fixing part.

In the liquid-administration device of the present invention, the connecting pipe is preferably configured such that a hematocrit tube can be fit inside of the pipe from the side of the pipe that is opposite to the needle.

In the liquid-administration device of the present invention, the protruding part is preferably flexible.

In the liquid-administration device of the present invention, the holding part includes two flaps that protrude in a direction perpendicular to the axis of the fixing part, and that are foldable so as to be parallel to each other.

In the liquid-administration device of the present invention, the holding part is configured as a single flap that protrudes in the direction perpendicular to the axis of the fixing part.

In the liquid-administration device of the present invention, each position of the fixing part and the needle is preferably such that the holding part by which the fixing part is held is opposite to the sharp part of the needle with respect to the axis of the fixing part.

The liquid-administration device of the present invention includes auxiliary-holding portions that are configured such that the portions protrude outward from the outer peripheral surface of the connecting pipe, and are capable of being held along with the holding part.

The liquid-administration device of the present invention allows for efficiently administering a liquid medicine to a small animal in a short time.

DETAILED DESCRIPTION

Hereinafter, embodiments and examples of the present invention will be described with reference to the accompanying drawings.

Figure 1:
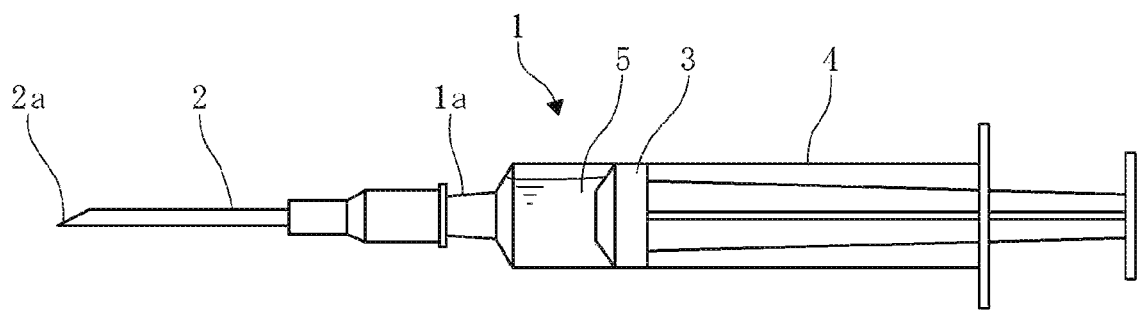
FIG. 1 is a side view showing an example of a conventional liquid-administration device.
Figure 2:
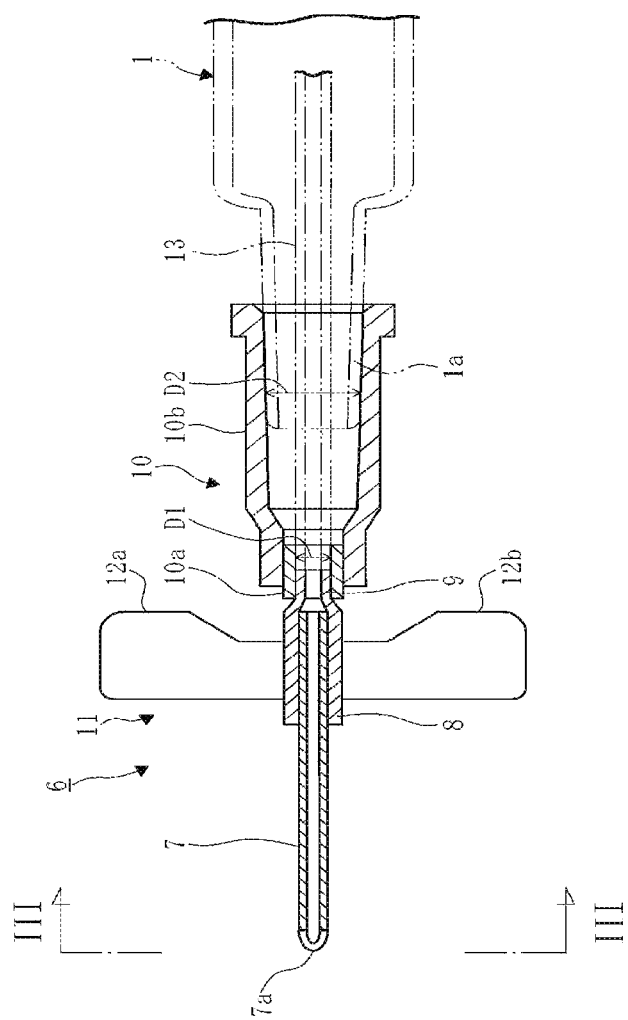
FIG. 2 is a top cross-sectional view showing an embodiment of a liquid-administration device according to the present invention.
Figure 3:
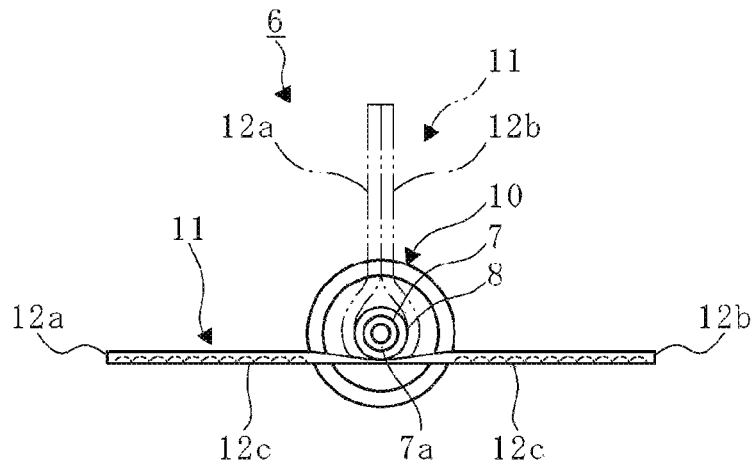
FIG. 3 is a front view that shows an embodiment of the liquid-administration device according to the present invention, and that corresponds to a cross-sectional view in the arrow direction of line of FIG. 2.

FIG. 2 and FIG. 3 show an embodiment of a liquid-administration device according to the present invention. The same reference numerals are used in the drawings as used in FIG. 1 for identical elements. A liquid-administration device 6 of the embodiment of the present invention includes, as shown in FIG. 2, (1) a hollow needle 7 to be injected into an object, (2) a cylindrical fixing part 8 having a small diameter that is fixed to the needle 7 so as to surround the outer periphery of the proximal end of the needle 7, (3) a connecting pipe 10 to be attached to a protruding part 9 that protrudes from the fixing part 8 to the side thereof that is opposite to the needle, and that is to be communicated with the needle 7, and (4) a holding part 11 that protrudes outward from the outer peripheral surface of the fixing part 8 in a direction away from the surface.

The fixing part 8 has an outer diameter that is about 2 times or more and about 4 times or less than the outer diameter of the needle 7, and, for example, has an outer diameter of 1.3 mm to 2.6 mm for a needle 7 that has an outer diameter of 0.65 mm.

The protruding part 9 of the fixing part 8 is flexible. For example, the flexible protruding part 9 can be formed such that the fixing part 8 is made of a soft synthetic resin, and the end portion of the fixing part 8 is made thinner than the main portion of the fixing part 8 so as to form the protruding part 9.

The connecting pipe 10 includes, as is shown in FIG. 2, (1) a first connecting portion 10a that is provided on the distal end of the connecting pipe 10, and (2) a second connecting portion 10b that is fixed to the first connecting portion 10a such that the second connecting portion 10b, which is cylindrical, surrounds the outer periphery of the proximal end of the first connecting portion 10a. As shown in FIG. 2, the first connecting portion 10a is connected to the protruding part 9 at the distal end thereof (the side facing the needle). The first connecting portion 10a has an inner diameter D1 that corresponds to the outer diameter of a hematocrit tube 13 that is shown by a virtual line on the proximal end side (the side opposite to the needle) of the first connecting portion 10a. In this way, the first connecting portion 10a is configured such that the hematocrit tube 13 can be inserted into the first connecting portion 10a from the side thereof that is opposite to the needle so as to be detachably fitted to the inside of the first connecting portion 10a. The second connecting portion 10b is connected to the first connecting portion 10a on the distal end of the second connecting portion 10b. The second connecting portion 10b has an inner diameter D2 that corresponds to the outer diameter of the distal end 1a of a syringe 1 that is shown by a virtual line on the proximal end of the second connecting portion 10b. In this way, the second connecting portion 10b is configured such that the distal end 1a of the syringe 1 can be inserted into the second connecting portion 10b from the side thereof that is opposite to the needle so as to be detachably fitted to the inside of the second connecting portion 10b. The protruding part 9 and the first connecting portion 10a, and the first connecting portion 10a and the second connecting portion 10b are respectively fixed to each other by using an adhesive.

Thus, the liquid-administration device 6 of the embodiment of the present invention is configured such that the hematocrit tube 13, in addition to the syringe 1, is connectable to the device 6 by using the connecting pipe 10 that is provided with the first connecting portion 10a and the second connecting portion 10b. As described later, the liquid-administration device 6 can be used also for drawing blood in addition to administering a liquid medicine.

The holding part 11 includes two flaps 12a and 12b that protrude in the direction perpendicular to the axis of the fixing part 8. As shown in FIGS. 2 and 3, the flaps 12a and 12b are provided to the fixing part 8 such that if the needle 7 is held horizontal, and the sharp part 7a of the needle 7 is positioned on the lower side of the needle 7, the flaps protrude horizontally from the fixing part 8. Antislip recesses and projections 12c are provided on the surfaces of the flaps 12a and 12b, the surfaces being the lower side of the flaps in this state of the device.

Each of the flaps 12a and 12b is flexible, and can be folded upward so as to enclose the fixing part 8, and for the flaps 12a and 12b to be parallel, as shown by a virtual line in FIG. 3, which allows the flaps 12a and 12b to be pinched while the device 6 is held. That is, when the device is used for injecting, which will be described later, if the flaps 12a and 12b are raised so that the surfaces on which the recesses and projections 12c are provided face outward, and the needle 7 is horizontally held, the sharp part 7a of the needle 7 is necessarily positioned on the lower side of the needle 7.

Figure 4:
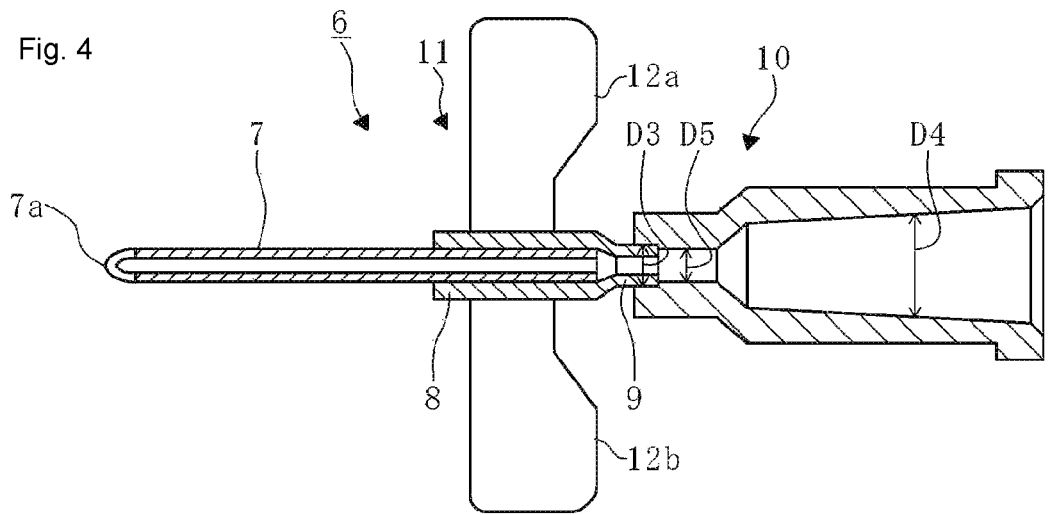
FIG. 4 is a top cross-sectional view showing another example of the embodiment of the liquid-administration device according to the present invention.

The configuration of the connecting pipe 10 is not limited to the aforesaid one. For example, instead of joining the first connecting portion 10a and the second connecting portion 10b that have been formed separately to form the connecting pipe 10 as shown in FIG. 2, the connecting pipe 10 may be integrally formed as shown in FIG. 4. In the connecting pipe 10 shown in FIG. 4, the inner diameter D3 of the portion on the most distal end of the connecting pipe 10, which corresponds to the first connecting portion 10a in FIG. 2, coincides with the outer diameter of the protruding part 9 of the fixing part 8. Also, the inner diameter D4 of the portion at the proximal end of the connecting pipe 10, which corresponds to the second connecting portion 10b in FIG. 2, coincides with the outer diameter of the distal end 1a of the syringe 1 in FIG. 2. Furthermore, the inner diameter D5 of the intermediate portion coincides with the outer diameter of the hematocrit tube 13 in FIG. 2. The protruding part 9 is fitted into the distal end of the connecting pipe 10 to be fixed thereto by using an adhesive. Also, the connecting pipe 10 is configured such that the distal end 1a of the syringe 1 in FIG. 2 or the hematocrit tube 13 in FIG. 2 is detachably fitted to the pipe 10 from the side thereof that is opposite to the needle. In addition, although the example of FIG. 4 shows that the inner diameter D3 is larger than the inner diameter D5, the inner diameter D3 and the inner diameter D5 may be such that the inner diameter D3 is smaller than the inner diameter D5, or the inner diameter D3 and the inner diameter D5 are equal to each other, in accordance with various conditions, including the size of the hematocrit tube 13 in FIG. 2.

Further, depending on the application of the liquid-administration device 6, the device 6 is not necessarily configured such that the hematocrit tube 13 can be fitted into the connecting pipe 10. That is, if the liquid-administration device 6 is not to be used for drawing blood, or if blood is drawn by using the syringe 1, as will be described later, the device 6 is not necessarily configured such that the hematocrit tube 13 is connectable. In such a case, the device 6 is sufficiently configured such that that only the syringe 1 is connectable.

Figure 5:
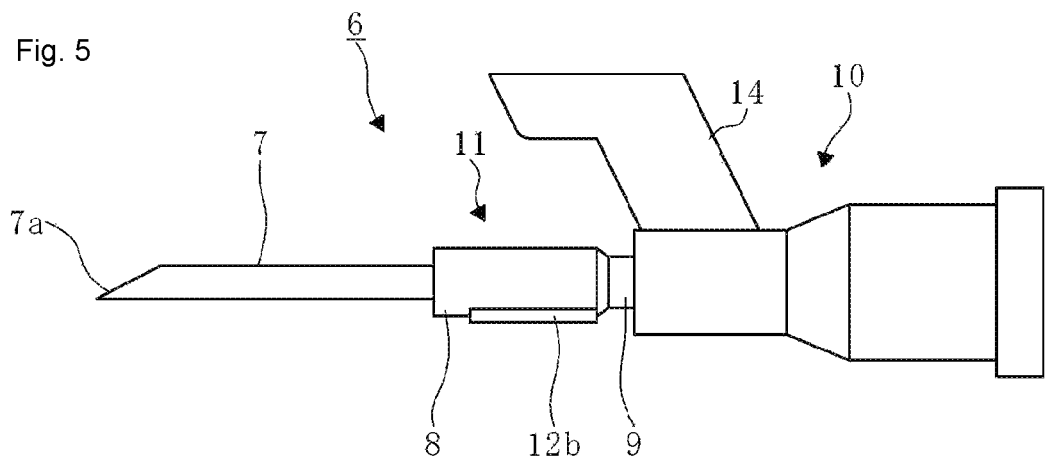
FIG. 5 is a side view showing yet another example of the embodiment of the liquid-administration device according to the present invention.

Moreover, as shown in FIG. 5, the device 6 can be provided with auxiliary-holding portions 14 that protrude outward from the outer peripheral surface of the connecting pipe 10 in addition to the holding part 11 of the fixing part 8. These auxiliary-holding portions 14 are flaps that extend in a direction away from the axis of the connecting pipe 10, and in the direction opposite to the sharp part 7a of the needle 7 with respect to the axis of the connecting pipe 10. The auxiliary-holding portions 14 formed as flaps are configured such that each of the flaps protrudes from the main body of the connecting pipe 10, and sticks out toward the distal end of the connecting pipe 10. When the holding part 11 is held as shown by the virtual line in FIG. 3, the auxiliary-holding portions 14 can be also held in a manner such that the portions 14 are sandwiched by the two flaps 12a and 12b.

Figure 6:
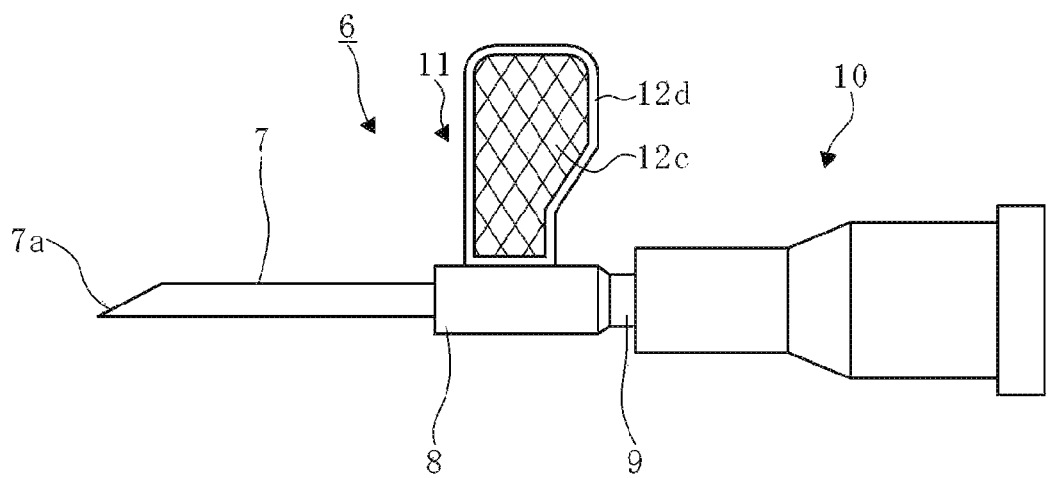
FIG. 6 is a side view showing yet another example of the embodiment of the liquid-administration device according to the present invention.

The configuration of the holding part 11 of the fixing part 8 is not limited to that shown in FIGS. 2 and 3. For example, as shown in FIG. 6, the holding part 11 can be configured as a single flap 12d that protrudes in the direction opposite to the sharp part 7a of the injection needle 7 with respect to the axis of the fixing part 8, the direction being perpendicular to the axis of the fixing part 8. Also in this example, recesses and projections 12c are provided on both surfaces of the flap 12d.

Next, the operation of the above-described embodiment will be described.

Figure 7:
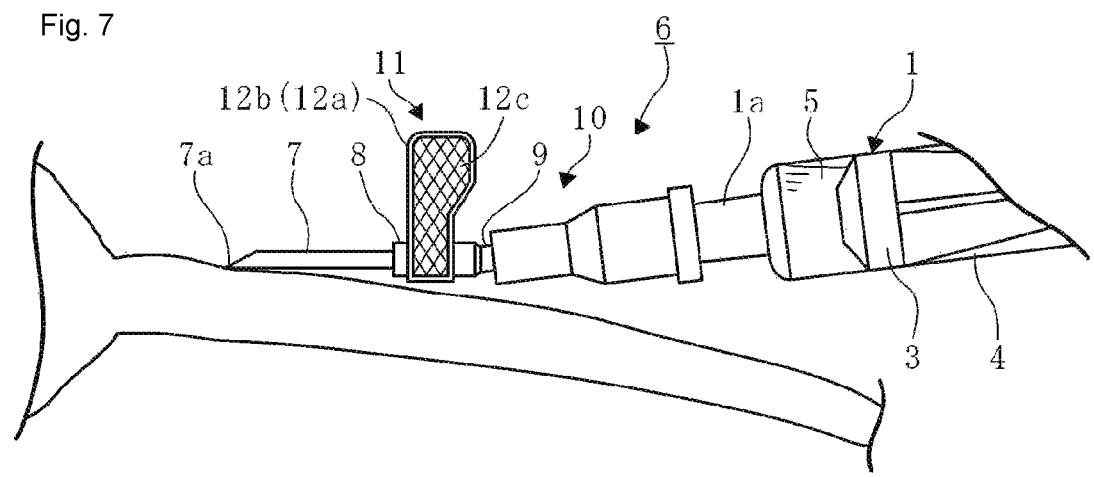
FIG. 7 is a side view showing the embodiment of the liquid-administration device in use according to the present invention.

FIG. 7 illustrates a case where a liquid medicine is administered to a small animal by using the above-described liquid-administration device 6. This case supposes an operation where intravenous liquid is administered to the tail of a mouse. The liquid-administration device 6 of the present invention can be used for other methods of administration, including subcutaneous administration, intraperitoneal administration, and intramuscular administration. Also, the liquid-administration device 6 is applicable to other small animals, including rats, rabbits, guinea pigs, and marmosets.

In administration, as shown in FIG. 7, (1) the holding part 11 consisting of the two flaps 12a and 12b is bent upward so as to enclose the fixing part 8, (2) the holding part 11 is firmly grasped between the thumb and forefinger, and (3) the needle 7 is held horizontally. At this time, each surface of the two flaps 12a and 12b, on which the recesses and projections 12c are provided, faces outward. In this way, the recesses and projections 12c prevent the thumb and forefinger from slipping.

Also, as described above, each position of the fixing part 8 and the needle 7 is fixed such that the holding part 11 by which the fixing part 8 is held is opposite to the sharp part 7a of the needle 7 with respect to the axis of the fixing part 8. Therefore, if the two flaps 12a and 12b are held in the manner as mentioned above, the sharp part 7a of the needle 7 is automatically positioned on the lower side of the needle 7. Accordingly, this eliminates the necessity of checking the position of the sharp part 7a in carrying out puncturing. That is, the recesses and projections 12c serve for positioning the device 6 in addition to preventing the device 6 from slipping when being injected.

In addition, if the liquid-administration device 6 that includes the auxiliary-holding portions 14 provided to the connecting pipe 10 as shown in FIG. 5 is used, the holding part 11 is held along with the auxiliary-holding portions 14. In this way, the connecting pipe 10 and the fixing part 8 can be simultaneously fixed with the thumb and forefinger, so that the entire liquid-administration device 6 can be more firmly held than in the examples without the auxiliary-holding portions 14 when injecting.

Also, if the liquid-administration device 6 that includes the holding part 11 consisting of the single flap 12d as shown FIG. 6 is used, it is sufficient to hold the holding part 11 such that the holding part 11 is to be on the upper side with respect to the needle 7. In this way, the sharp part 7a of the needle 7 is automatically positioned on the lower side of the needle 7, which is the correct position for injecting.

While the holding part 11 is held, the needle 7 is horizontally injected at an appropriate position of the object (in this case, the tail of a mouse), and a drug solution 5 is injected from the syringe 1 that is connected to the connecting pipe 10. In this way, in the state where the entire liquid-administration device 6, including the needle 7, is firmly held with the holding part 11, the needle 7 can be injected at a target region at a shallow angle. Thus, for example, in the case of intravenous administration to a small animal, aligning the tip of the needle 7 with a small vein is easily accomplished. Therefore, the administration to a small animal can be easily carried out in a short time without requiring experience and skill on the part of a user.

Also, while the needle 7 is horizontally held during administration, the protruding part 9, which is flexible, can be bent upward, by which the side of the syringe 1, the side being opposite to the needle, with the syringe 1 being connected to the liquid-administration device 6, can be raised with regard to the object into which the needle 7 is to be injected. By adjusting the position of the syringe 1 in this manner, the puncture angle can be made shallower than conventional devices at the time of administration, and to align the tip of the needle 7 with the object into which liquid is to be administered becomes easier.

Further, the liquid-administration device 6 of the embodiment of the present invention is configured such that the hematocrit tube 13 can be connected to the connecting pipe 10 as described above (see FIG. 2) in addition to being connected to the syringe 1. Thus, the liquid-administration device 6 is applicable both to administration of a drug solution and to drawing blood by using the hematocrit tube 13. Blood can be withdrawn efficiently and conveniently by the same procedures as described above. While blood is being withdrawn, the protruding part 9 is preferably bent downward so that the side of the hematocrit tube 13, the side being opposite to the needle, is lowered, contrary to the administration of a drug solution as mentioned above. In this way, suction due to capillary action by the hematocrit tube 13 is enhanced by gravity, which can reduce the time required for drawing blood.

Further, even in the case where the liquid-administration device 6 is not configured such that the hematocrit tube 13 (see FIG. 2) is connectable, the device 6 is able to appropriately carry out blood drawing by using a syringe 1.

As is described above, the embodiment of the present invention includes (1) a hollow needle 7, (2) a fixing part 8 that is fixed on the outer periphery of the proximal end of the needle 7, (3) a connecting pipe 10 to be attached to the protruding part 9 that protrudes from the fixing part 8 to the side thereof that is opposite to the needle, and that can be communicated with the needle 7, wherein the pipe 10 is configured such that the distal end 1a of the syringe 1 can be fitted to the pipe 10 from the side thereof that is opposite to the needle, and (4) a holding part 11 that protrudes outward from the outer peripheral surface of the fixing part 8. Thus, a drug solution can be conveniently administered to a small animal by holding the holding part 11 for the needle 7 to be injected at a target region, and for the drug solution 5 to be injected from the syringe 1.

Also, in the embodiment of the present invention, the connecting pipe 10 is configured such that the hematocrit tube 13 is fittable to the pipe 10 from the side thereof that is opposite to the needle. Thus, the liquid-administration device 6 is also applicable to drawing blood by using the hematocrit tube 13.

Also, in the embodiment of the present invention, the protruding part 9 is flexible. Therefore, by bending the protruding part 9, the position of each of the components, such as the syringe 1 or the hematocrit tube 13 that is to be connected to the liquid-administration device 6, can be adjusted, which makes it easy to administer a liquid drug or to draw blood.

Also, in the embodiment of the present invention, the holding part 11 can be configured as two flaps 12a and 12b, each of which protrudes in a direction perpendicular to the axis of the fixing part 8, and each of which is foldable so as to be parallel to t other. This configuration of the holding part 11 allows for firm holding of the liquid-administration device 6.

Also, in the embodiment of the present invention, the holding part 11 can be configured as a single flap 12d that protrudes in the direction perpendicular to the axis of the fixing part 8. This configuration of the holding part 11 also allows for the liquid-administration device 6 to be held firmly.

Also, in the above embodiment of the present invention, each position of the fixing part 8 and the needle 7 is fixed such that the holding part 11 by which the fixing part 8 is held is opposite to the sharp part 7a of the needle 7 with respect to the axis of the fixing part 8. Accordingly, if the holding part 11 is held, the sharp part 7a of the needle 7 is automatically positioned on the lower side of the needle 7, which allows for easy positioning of the needle 7 when inserting the needle 7.

Also, in the above embodiment of the present invention, the device 6 can be provided with auxiliary-holding portions 14 that are configured such that the portions 14 protrude outward from the outer peripheral surface of the connecting pipe 10, and can be held along with the holding part 11. This configuration allows for the liquid-administration device 6 to be held even more firmly.

Accordingly, the above embodiment of the present invention allows for efficiently administering a liquid medicine to a small animal in a short time.

While a particular embodiment and examples of the present invention have been shown and described with reference to the drawings, it will be appreciated by those skilled in the art that changes and modifications may be made thereto without departing from the invention in its broader aspects.

DESCRIPTION OF REFERENCE NUMERALS 1. syringe
1a. distal end
6. liquid-administration device
7. needle
7a. sharp part
8. fixing part
9. protruding part
10. connecting pipe
11. holding part
12a. flap
12b. flap
12d. flap
13 hematocrit tube
14. auxiliary-holding portions

The invention claimed is:

1. A liquid-administration device comprising:
a hollow needle;
a fixing part that surrounds and is fixed to the outer periphery of the proximal end of the needle;
a connecting pipe attached to a protruding part that protrudes from the fixing part to the side thereof that is opposite to the needle, and in communication with the needle, the connecting pipe being configured such that a distal end of a syringe and a hematocrit tube are fittable to the pipe from the side that is opposite to the needle; and
a holding part that protrudes outward from the outer peripheral surface of the fixing part;
wherein the connecting pipe comprises a first connecting portion on the distal end thereof and a second connecting portion on the proximal end of the first connecting portion,
wherein the first connecting portion is connected to the protruding part at the distal end thereof, and has an inner diameter that corresponds to the outer diameter of the hematocrit tube, the hematocrit tube being inserted in the first connecting portion from the side opposite to the needle to be detachably fitted to the inside of the first connecting portion, and
wherein the second connecting portion is connected to the first connecting portion on the distal end thereof, and has an inner diameter that corresponds to the outer diameter of the distal end of the syringe on the proximal end thereof, the distal end of the syringe being inserted in the second connecting portion from the side opposite to the needle to be detachably fitted to the inside of the second connecting portion.

2. The liquid-administration device of claim 1, wherein the protruding part is flexible.

3. The liquid-administration device of claim 1, wherein the holding part includes two flaps that protrude in a direction perpendicular to the axis of the fixing part, and that are foldable so as to be parallel to each other.

4. The liquid-administration device of claim 3, further comprising auxiliary-holding portions that protrude outward from the outer peripheral surface of the connecting pipe, and that are capable of being held along with the holding part.

5. The liquid-administration device of claim 3, wherein each position of the fixing part and the needle is fixed such that the holding part by which the fixing part is held is opposite to the sharp part of the needle with respect to the axis of the fixing part.

6. The liquid-administration device of claim 5, further comprising auxiliary-holding portions that protrude outward from the outer peripheral surface of the connecting pipe, and that are capable of being held along with the holding part.

7. The liquid-administration device of claim 1, wherein the holding part is configured as a single flap that protrudes in the direction perpendicular to the axis of the fixing part.

8. The liquid-administration device of claim 7, wherein each position of the fixing part and the needle is fixed such that the holding part by which the fixing part is held is opposite to the sharp part of the needle with respect to the axis of the fixing part.

\* \* \* \* \*